(12) United States Patent
Barney et al.

(10) Patent No.: US 7,005,453 B1
(45) Date of Patent: Feb. 28, 2006

(54) **USE OF HOP ACIDS TO INHIBIT GROWTH OF *STAPHYLOCOCCUS AUREUS* AND PREVENT TOXIC SHOCK SYNDROME**

(75) Inventors: Michael C. Barney, Elm Grove, WI (US); Alfonso L. Navarro, Valencia (ES); David S. Ryder, Mequon, WI (US)

(73) Assignee: Miller Brewing Company, Milwaukee, WI (US)

( * ) Notice: Subject to any disclaimer, the term of this patent is extended or adjusted under 35 U.S.C. 154(b) by 0 days.

(21) Appl. No.: 09/664,519

(22) Filed: Sep. 18, 2000

Related U.S. Application Data

(60) Provisional application No. 60/158,810, filed on Oct. 12, 1999.

(51) Int. Cl.
*A61K 31/12* (2006.01)

(52) U.S. Cl. .................. 514/690; 435/883; 424/405; 424/175.1; 424/9.1; 568/315; 568/316

(58) Field of Classification Search ............ 424/175.1, 424/405, 9.1; 568/315, 316; 514/690; 435/883
See application file for complete search history.

(56) References Cited

U.S. PATENT DOCUMENTS

| | | | |
|---|---|---|---|
| 3,001,201 A | 9/1961 | Hauser | |
| 3,490,454 A | 1/1970 | Goldfarb et al. | |
| 3,896,807 A | 7/1975 | Buchalter | |
| 3,905,372 A | 9/1975 | Denkinger | |
| 3,923,897 A | 12/1975 | Worden | |
| 4,002,683 A | 1/1977 | Todd, Jr. | |
| 4,226,232 A | 10/1980 | Spence | |
| 4,259,383 A | 3/1981 | Eggensperger et al. | |
| 4,431,427 A | 2/1984 | Lefren et al. | |
| 4,564,362 A | 1/1986 | Burnhill | |
| 4,585,792 A | 4/1986 | Jacob et al. | |
| 4,783,340 A | 11/1988 | McDonell et al. | |
| 4,842,593 A | 6/1989 | Jordan et al. | |
| 4,848,572 A | 7/1989 | Herrera | |
| 5,082,975 A * | 1/1992 | Todd, Jr. et al. | ............ 568/315 |
| 5,201,326 A | 4/1993 | Kubicki et al. | |
| 5,252,580 A | 10/1993 | Takahashi et al. | |
| 5,260,066 A | 11/1993 | Wood et al. | |
| 5,273,521 A | 12/1993 | Peiler et al. | |
| 5,336,500 A | 8/1994 | Richter et al. | |
| 5,350,067 A | 9/1994 | Beltran | |
| 5,389,374 A | 2/1995 | Brown-Skrobot | |
| 5,393,528 A | 2/1995 | Staab | |
| 5,419,908 A | 5/1995 | Richter et al. | |
| 5,455,038 A | 10/1995 | Barney et al. | |
| 5,466,462 A | 11/1995 | Rosenthal et al. | |
| 5,584,801 A | 12/1996 | Kuroyanagi et al. | |
| 5,600,012 A | 2/1997 | Poyner et al. | |
| 5,612,045 A | 3/1997 | Syverson | |
| 5,685,872 A | 11/1997 | Syverson | |
| 5,817,047 A | 10/1998 | Osborn, III et al. | |
| 5,827,895 A | 10/1998 | Nutter et al. | |

FOREIGN PATENT DOCUMENTS

| | | |
|---|---|---|
| EP | 0 606 599 A1 | 7/1994 |
| WO | WO 98/11883 | 3/1998 |
| WO | 9811883 * | 9/1998 |

\* cited by examiner

*Primary Examiner*—Kathleen M. Kerr
*Assistant Examiner*—Chih-Min Kam
(74) *Attorney, Agent, or Firm*—Quarles & Brady LLP

(57) ABSTRACT

The present invention provides methods, products, and compositions for selectively inhibiting the growth of *Staphylococcus aureus* without preventing the growth of *Lactobacillus* species. Specifically, the present invention discloses the use of tetrahydroiso alpha acid or hexahydro beta acid at a concentration effective to inhibit the growth of *S. aureus* without preventing the growth of *Lactobacillus*. The inhibition of *S. aureus* in accordance with the present invention thus provides useful methods, compositions and products such as feminine hygiene products for treating the diseases associated with *S. aureus* infections and infestations, i.e., toxic shock syndrome, without disrupting the normal bacterial flora in the area of its application.

9 Claims, No Drawings

USE OF HOP ACIDS TO INHIBIT GROWTH OF *STAPHYLOCOCCUS AUREUS* AND PREVENT TOXIC SHOCK SYNDROME

CROSS-REFERENCE TO RELATED APPLICATIONS

This application claims priority from provisional patent application Ser. No. 60/158,810, filed Oct. 12, 1999.

STATEMENT REGARDING FEDERALLY SPONSORED RESEARCH OR DEVELOPMENT

Not applicable.

BACKGROUND OF THE INVENTION

The present invention relates to the use of compounds to affect the growth of certain bacterial species. More specifically, the present invention relates to the use of tetrahydroiso alpha acids or hexahydro beta acids at concentrations effective to kill, inhibit, or otherwise control the growth or proliferation of *Staphylococcus aureus* without preventing the growth of *Lactobacillus*. The inhibition of *S. aureus* in accordance with the present invention thus provides useful products, compositions and methods for treating the diseases associated with *S. aureus* infections and infestations, i.e. toxic shock syndrome, without disrupting the normal bacterial flora in the area of its application.

A commonly known disease caused by *S. aureus* is toxic shock syndrome (TSS). TSS is a severe, toxin-induced disease arising from the exposure to the *S. aureus* toxin called toxic shock syndrome toxin-1 (TSST-1) (Iandolo, *Ann. Rev. of Micro.* 43:275–402, 1989). The disease is characterized by a sudden onset of symptoms, including high fever, chills, rash, vomiting or diarrhea, and a rapid drop in blood pressure leading to shock.

Toxic shock syndrome has been reported to occur in both men and women of all ages, with approximately two cases occurring annually per 10,000 people. TSS, however, is most commonly seen in menstruating women in whom the primary site of infection is the vagina. Epidemiological evidence especially suggests that women who use highly absorbent tampons incur an increased risk for developing the disease as the highly absorbent tampon serves as an suitable environment for *S. aureus* growth. TSS has also been reported to occur in infants, children, men, and non-menstruating women, but at a lower frequency. These cases are generally not associated with the use of tampons, but result from skin wounds or infections in other parts of the body. The use of barrier contraceptives has also been implicated as another risk factor.

Because of the sudden onset of the disease, persons suffering from TSS may not receive appropriate medical intervention before serious complications result. Such complications may include kidney failure, heart failure, liver failure and profound shock. Accordingly, there is a very strong emphasis on disease prevention. For example, women are cautioned against using high absorbency tampons. However, many women are not willing to sacrifice the comfort and convenience of using high absorbency tampons for what they perceive to be a remote risk of developing TSS. Therefore, considerable effort has been directed toward developing new tampons capable of reducing the risk of contracting TSS as compared to conventional tampons.

Various approaches for preventing toxic shock syndrome from tampon use have been advanced. One such method includes incorporating bactericidal or bacteriostatic agents (i.e., antibiotics or phenol) into the tampon to inhibit *S. aureus* growth. Other methods include the incorporation of agents which prevent the production of TSST-1 or inactivate TSST-1. For example, U.S. Pat. No. 4,405,323 discloses the incorporation of an antibacterial agent, such as povione-iodine, mercury, zinc, penicillin, erythromycin, and nitrofurazone, within a tampon to prevent TSS. U.S. Pat. No. 4,431,427 discloses the incorporation of a water-soluble acid (i.e., citric, glycolic, malic, tartaric, or lactic acid) in a tampon at an amount sufficient to maintain a pH of 4.5 or less in the fluids absorbed by the tampon so as to inhibit the growth of pathogenic bacteria. PCT publication WO 86/05388 discloses that the inclusion of a nontoxic divalent cation, such as magnesium, barium, calcium, strontium, or the like, in an absorptive pad has the effect of inhibiting the production of TSST-1 by *S. aureus*. U.S. Pat. No. 4,585,792 discloses that L-ascorbic acid may be delivered on a tampon to the vaginal area so as to inactivate the toxins associated with TSS. U.S. Pat. No. 5,389,374 discloses that the production of *S. aureus* enterotoxins can be inhibited by exposing the bacterium to an absorbent material treated with either a mono- or diester of apolyhydric aliphatic alcohol.

Although the use of some of these approaches have proven effective in inhibiting the growth of *S. aureus* and TSS, their use may also be problematic. For example, exposing a bacterial population to antibiotics may select for antibiotic resistant mutants, and decrease the efficacy of the antibiotic in treating future infections. In addition, the inclusion of conventional antibiotics will likely result in a considerable increase in cost to the consumer. Moreover, the use of antibiotics or other bactericidal or bacteriostatic agents may have the undesirable effect of disrupting the normal bacterial flora present in their area of application, ultimately resulting in the onset of other bacterial infections and diseases. For example. *Lactobacillus* is one of the predominant bacteria among normal vaginal flora. The administration of a compound which inhibits *Lactobacillus* may also have the added affect of promoting the establishment of other, less desirable microorganisms which are also present in the vagina. For instance, a low number of *Candida albicans* may be present in the vagina of many healthy asymptomatic women. The administration of a compound which inhibits the growth of *Lactobacillus* may also have the added affect of allowing *C. albicans* to grow and predominate, resulting in a yeast infection.

It would be advantageous, therefore, to have a method for preventing TSS which does not affect normal bacterial flora, and does not allow for the selection of antibiotic resistant bacteria, and does not result in a substantial increase in the overall cost to the consumer. In particular, what is needed is a relatively inexpensive method for inhibiting the growth of *S. aureus* without preventing the growth of *Lactobacillus* or other normal microflora.

BRIEF SUMMARY OF THE INVENTION

The present invention is summarized in that certain compounds are disclosed which are capable of affecting the growth of *Staphylococcus aureus* without preventing the growth of *Lactobacillus* when applied in certain concentrations. These compounds are selected from the group consisting of tetrahydroiso alpha acids, hexahydro beta acids, and salts, mixtures or combinations thereof, and are applied in an amount effective to kill, inhibit, or otherwise control the growth or proliferation of *S. aureus* without preventing the growth of *Lactobacillus*. An effective amount of such compounds, for example, includes a concentration in the range of from about 0.2 ppm to about 25 ppm, or more preferably in the range of from about 0.5 ppm to about 12.5 ppm.

In addition, the present invention includes a product comprising an absorbent material and a compound selected from the group consisting of tetrahydroiso alpha acids, hexahydro beta acids, salts thereof, and mixtures thereof in an amount effective to kill, inhibit, or otherwise control the growth or proliferation of *S. aureus* without preventing the growth of *Lactobacillus*. The material may include, for example, cellulosic fiber material such as those typically used in feminine hygiene products (i.e., feminine napkins, tampons, etc.), or used to absorb bodily fluids or apply compounds employed in preventing or treating bacterial infections.

The present invention also includes a composition comprising a pharmaceutically acceptable carrier, and a compound selected from the group consisting of tetrahydroiso alpha acids, hexahydro beta acids, salts thereof, and mixtures thereof in an amount effective to kill, inhibit, or otherwise control the growth or proliferation of *S. aureus* without preventing the growth of *Lactobacillus*. The carrier may include, for example, topical ointments or washes formulated to facilitate effective administration of the compound.

It is an object of the present invention to provide a compound having inhibitory activity against *S. aureus* and minimal to no inhibitory activity against *Lactobacillus* when applied at certain concentrations.

It is also an object of the present invention to provide products and compositions for contacting *S. aureus* with such a compound.

It is yet another object of the invention to provide a method for preventing or treating *S. aureus* infection or infestation.

Other objects, advantages and features of the present invention will become apparent from the following detailed description and examples.

BRIEF DESCRIPTION OF THE SEVERAL VIEWS OF THE DRAWINGS

Not applicable.

DETAILED DESCRIPTION OF THE INVENTION

The present invention discloses compounds which, when applied at certain concentrations, affect the growth of *Staphylococcus aureus* without preventing the growth of *Lactobacillus*. The compounds are selected from the group consisting of tetrahydroiso alpha acids, hexahydro beta acids, salts thereof, and mixtures thereof, and may be combined with various materials or carriers to form products and compositions suitable for facilitating effective administration. The present invention also discloses methods for using the compounds to prevent or treat *S. aureus* infection or infestation without disrupting the normal flora of *Lactobacillus* in its area of application.

We have discovered that the hop acids tetrahydroiso alpha and hexahydro beta have unexpectedly different bacteriocidal or bacteriostatic effects against *Lactobacillus* as compared to *S. aureus*. Specifically, *Lactobacillus* and *S. aureus* exhibit a differing level of sensitivity to tetrahydroiso alpha and hexahydro beta acids, with *S. aureus* being more sensitive than *Lactobacillus*. As a result, it is now possible to selectively inhibit *S. aureus* without preventing the growth of *Lactobacillus* by contacting the *S. aureus* with an amount of tetrahydroiso alpha acid or hexahydro beta acid which effectively inhibits *S. aureus* while allowing *Lactobacillus* to continue to grow.

The primary embodiment of the present invention is to provide a method for inhibiting *S. aureus* infection or infestation by contacting the *S. aureus* environment with an effective concentration of a compound which kills, inhibits, or otherwise controls the growth or proliferation of *S. aureus* without preventing the growth of *Lactobacillus*. In the preferred embodiment, the *S. aureus* environment is exposed to an effective concentration of the compound in a range of from about 0.2 ppm to about 25 ppm, and more preferably, in a range of from about 0.5 ppm to about 12.5 ppm.

As used herein, the term "compound" is intended to include hexahydro beta acids, hexahydro beta salts, tetrahydroiso alpha acids, tetrahydroiso alpha salts, and mixtures or combinations thereof.

To affect the growth of *S. aureus* the compound may be placed in contact with a *S. aureus* environment either independently or as part of a composition or product wherein the composition or product contains an effective amount of the compound in accordance with the present invention. In another embodiment, the compound may be layered or coated onto a barrier type contraceptive such as a diaphragm or contraceptive sponge that is placed in the *S. aureus* environment. The *S. aureus* environment may include, for example, any environment having a population of the *S. aureus* bacterium or an environment capable of allowing *S. aureus* to grow and proliferate. For instance, the environment may include, without limitation, wounds, lesions, tampons, the vagina, sanitary napkins, gauze, diapers, suppositories, or any other possible areas susceptible to *S. aureus* infection or infestation.

As used herein, the term "product" includes those products capable of, either inherently or by virtue of the manner in which they are assembled, absorbing liquids such as water, urine, menstrual fluids, blood, wound exudates and the like. Such products include, for example, catemenial products (e.g. tampons), wound dressings, suppositories, disposable diapers, and sanitary napkins, in addition to other kinds of tampons intended for medical, surgical, dental and/or nasal use. Products according to the present invention may be prepared according to known methods for manufacturing such products. In general, the products should be prepared to allow an effective amount of the compound utilized to be placed in contact with the *S. aureus* environment.

In one embodiment, the product comprises of an absorbent material and an amount of compound which effectively kills, inhibits, or otherwise controls the growth or proliferation of *S. aureus* without preventing the growth of *Lactobacillus* when said product is exposed to the *S. aureus* environment. A used herein, the term "absorbent material" includes, without limitation, natural fibers or synthetic fibers, films, foams, wood, pulp, peat moss, superabsorbent polymers and the like which are capable of, either inherently or by virtue of the manner in which they are assembled, absorbing liquids such as water, urine, menstrual fluids, blood, wound exudates and the like.

The term "composition" includes those compositions capable of, either inherently or by virtue of their formulation, use as a topical ointment or wash applied to a wound, infection, or the like. Compositions may be formulated according to known methods for preparing pharmaceutically useful compositions. Formulations are described in detail in a number of sources which are well known and readily available to those skilled in the art. For example, *Remington's Pharmaceutical Science*, by E. W. Martin describes formulations which can be used in connection with the subject invention. In general, the compositions should be formulated such that an effective amount of the compound utilized is combined with the suitable carrier in order to facilitate effective administration.

In one embodiment, the composition consists of a douche for killing, inhibiting, or otherwise controlling the growth or proliferation of *S. aureus* in the vagina. This is particularly useful for providing a treatment to a woman to help fight against *S. aureus* infection or infestation that can cause toxic shock syndrome. Alternatively, the composition may be formulated as a topical ointment or wash for application to wounds or infections in other parts of the body.

It should be understood that the examples and embodiments described herein are for illustrative purposes only and that various modifications or changes in light thereof are to be included within the spirit and purview of this application and the scope of the appended claims. Following are examples which are intended to be purely illustrative, and should not be construed as limiting but merely exemplary.

EXAMPLES

Minimal inhibitory concentration (MIC) assays of several hop compounds were conducted using a *Staphylococcus aureus* species and vaginal isolates *Lactobacillus vaginalias, Lactobacillus crispatus, Lactobacillus gasseri,* and *Lactobacillus jensenii* as test microorganisms. *Lactobacillus* assays were conducted in *Lactobacillus* MRS broth (Difco) tubes. A 0.1 ml aliquot of a 1% (w/w) solution of each hop acid in alcohol was added to a tube of sterile MRS broth to give a final concentration of 100 ppm of the hop. This solution was serially diluted in tubes with sterile MRS broth using a two-fold dilution series. A second dilution series prepared as above, but using 0.1 ml alcohol without hop acid, was used as a positive control of bacterial growth. Each tube was inoculated with a fresh culture ($10^4$ cells) of a *Lactobacillus* species in MRS broth. The cultures were incubated anaerobically in a $CO_2$ incubator at 28° C. for five days. Growth was evaluated by visually assessing and scoring development of turbidity in the tube of broth.

The MIC assays for *Staphylococcus aureus* were conducted in Difco trypticase soy broth (TSB) using the same serial dilution technique and the inoculum level as described above. The pH of the TSB was adjusted to pH7.0, pH 6.0, or pH5.0 using hydrochloric acid. The tubes were incubated aerobically at 37° C. for three days and growth was evaluated by visually assessing and scored the development of turbidity in the broth.

The results of MIC assay of tetrahydroiso alpha acids and hexahydro beta acids on *S. aureus* and *Lactobacillus* are shown in Tables 1 and 2, respectively. As illustrated by a comparison of Tables 1 and 2, it is evident that *S. aureus* is much more sensitive to tetrahydroiso alpha acids and hexahydro beta acids than the *Lactobacillus* species tested. In particular, *Lactobacillus* exhibited strong growth in concentrations of hexahydro beta acid and tetrahydroiso alpha acid as high as 12.5 ppm. In contrast, *S. aureus* showed no to very weak growth in tetrahydroiso alpha acid or hexahydro beta acid concentrations as low as 1.56 ppm. The sensitivity of *S. aureus* also appeared to increase under acidic conditions, with the minimum inhibitory concentration decreasing to 0.78 ppm at pH 6.0 and to less than 0.2 ppm at pH 5.0. Normally, the pH of the vagina is in the range of about 4.5 to 5.0.

TABLE 1

MIC Assays of Tetrahydroiso Alpha Acids and Hexahydro Beta Acids using *Staphylococcus aureus*

| Concentration (ppm) | TSB at pH 7.0 | | TSB at pH 6.0 | | TSB at pH 5.0 | |
|---|---|---|---|---|---|---|
| | Tetra | Hexa | Tetra | Hexa | Tetra | Hexa |
| 100 | No growth | No growth | No growth | No growth | No growth | No growth |
| 50 | No growth | No growth | No growth | No growth | No growth | No growth |
| 25 | No growth | No growth | No growth | No growth | No growth | No growth |
| 12.5 | No growth | No growth | No growth | No growth | No growth | No growth |
| 6.25 | No growth | No growth | No growth | No growth | No growth | No growth |
| 3.125 | No growth | No growth | No growth | No growth | No growth | No growth |
| 1.56 | +/− Growth | +/− Growth | No growth | No growth | No growth | No growth |
| 0.78 | + Growth | + Growth | No growth | No growth | No growth | No growth |
| 0.39 | ++ Growth | ++ Growth | +/− Growth | No growth | No growth | No growth |
| 0.2 | +++ Growth | +++ Growth | ++ Growth | + Growth | No growth | No growth |
| 0 | +++ Growth | +++ Growth | +++ Growth | +++ Growth | +++ Growth | +++ Growth |

TABLE 2

MIC Assays of Tetrahydroiso Alpha Acids and Hexahydro Beta Acids using *Lactobacillus* species

| Concentration (ppm) | MRS at pH 6.3 | |
|---|---|---|
| | Tetra | Hexa |
| 100 | No growth | No growth |
| 50 | No growth | No growth |
| 25 | +/− Growth | +/− Growth |
| 12.5 | ++ Growth | +++ Growth |
| 6.25 | +++ Growth | +++ Growth |
| 3.125 | +++ Growth | +++ Growth |
| 1.56 | +++ Growth | +++ Growth |
| 0.78 | +++ Growth | +++ Growth |
| 0.39 | +++ Growth | +++ Growth |
| 0.2 | +++ Growth | +++ Growth |
| 0 | +++ Growth | +++ Growth |

We claim:

1. A method for affecting the growth of *Staphylococcus aureus* in the vaginal area, said method comprising the step of:

contacting the vaginal area with a compound selected from the group consisting of hexahydro beta acids, hexahydro beta salts, tetrahydroiso alpha acids, and tetrahydroiso alpha salts, in an amount effective to kill, inhibit, or otherwise control the growth or proliferation of *S. aureus* in the vaginal area while allowing the growth of *Lactobacillus* in the vaginal area wherein the concentration of the compound is in the range of from about 0.2 ppm to about 25 ppm.

2. The method of claim 1, wherein the compound is placed in contact with the vaginal area using a product comprising an absorbent material and the compound.

3. The method of claim 2, wherein the absorbent material is selected from the group consisting of a natural fiber, a synthetic fiber, a film, a foam, a wood, a pulp, a peat moss, and a superabsorbent polymer.

4. The method of claim 2, wherein the product is selected from the group consisting of a tampon, suppository, disposable diaper, and sanitary napkin.

5. The method of claim 1, wherein the compound is placed in contact with the vaginal area using a composition comprising of a pharmaceutically acceptable carrier and the compound.

6. The method of claim 5, wherein the compound is either in a douche or in a topical ointment.

7. The method of claim 1, wherein the compound is placed in contact with the vaginal area using a barrier contraceptive.

8. A product for affecting the growth of *Staphylococcus aureus* in the vaginal area, the product comprising an absorbent material, and a compound selected from the group consisting of hexahydro beta acids, hexahydro beta salts, tetrahydroiso alpha acids, and tetrahydroiso alpha salts, in an amount effective to kill, inhibit, or otherwise control the growth or proliferation of *S. aureus* in the vaginal area while allowing the growth of *Lactobacillus* in the vaginal area wherein the concentration of the compound is in the range of from about 0.2 ppm to about 25 ppm.

9. The product of claim 8, wherein the absorbent material is selected from the group consisting of a natural fiber, a synthetic fiber, a film, a foam, a wood, a pulp, a peat moss, and a superabsorbent polymer.

* * * * *